(12) United States Patent
Contarino

(10) Patent No.: US 7,163,321 B2
(45) Date of Patent: Jan. 16, 2007

(54) EMERGENCY VEHICLE GRILLE

(76) Inventor: Steven Contarino, 1 Autumn Ln, Methuen, MA (US) 01844

( * ) Notice: Subject to any disclaimer, the term of this patent is extended or adjusted under 35 U.S.C. 154(b) by 0 days.

(21) Appl. No.: 10/622,248

(22) Filed: Jul. 18, 2003

(65) Prior Publication Data

US 2004/0057242 A1    Mar. 25, 2004

Related U.S. Application Data

(60) Provisional application No. 60/399,039, filed on Jul. 25, 2002.

(51) Int. Cl.
*F21W 101/02* (2006.01)
(52) U.S. Cl. .................... 362/496; 362/540; 362/542
(58) Field of Classification Search ............. 362/496, 362/487, 542, 540, 543–545
See application file for complete search history.

(56) References Cited

U.S. PATENT DOCUMENTS

| 5,373,426 A | * | 12/1994 | O'Sullivan | 362/496 |
| 6,238,070 B1 | * | 5/2001 | Galliner et al. | 362/505 |
| 6,357,707 B1 | * | 3/2002 | Lindsay | 248/226.11 |

FOREIGN PATENT DOCUMENTS

| JP | 357178946 A | * | 11/1982 |
| JP | 362094450 A | * | 4/1987 |

* cited by examiner

*Primary Examiner*—Laura K. Tso
(74) *Attorney, Agent, or Firm*—Paul C. Remus; Devine, Millimet & Branch

(57) ABSTRACT

The present invention is an inconspicuous emergency vehicle grille designed with emergency lights built flush therein thereby allowing the lights to be unobstructed by the grille and conspicuous when lit. This invention further provides the opportunity to retrofit the emergency vehicle grille with minimal effort by simply replacing the existing grille with a new grille prefabricated with the emergency lights. Alternatively, this invention is an emergency vehicle grille designed with emergency light sockets for the installation of flush mounted emergency lights.

7 Claims, 1 Drawing Sheet

EMERGENCY VEHICLE GRILLE

The present application claims priority based on Provisional Application Ser. No. 60/399,039, which was filed Jul. 25, 2002.

FIELD OF THE INVENTION

The present invention relates to automotive parts. Specifically, the present invention relates to automotive parts for emergency vehicles. More specifically, the present invention relates to emergency lights for emergency vehicles.

BACKGROUND OF THE INVENTION

The present invention relates to emergency vehicles, primarily police vehicles. For years, police vehicles have employed flashing blue emergency lights conspicuously located on the top of the vehicle. During an emergency situation, the driver turns the flashing lights on, clearly signifying to the surrounding drivers, pedestrians, and other nearby individuals to clear a path to permit the emergency vehicle to race to the emergency. The problem with this type of vehicle, for some emergency personnel, is the location of the lights makes it difficult for the vehicle to be inconspicuous in non-emergency situations.

More recently, emergency vehicles designed to be inconspicuous in non-emergency situations have been devised. One design has been to locate the emergency lights behind the grille, which makes it difficult to identify the emergency vehicle until the flashing emergency lights are started. The problem with this design is, due to the obstruction of the grille, the lights are not very conspicuous when started. Because the lights are not conspicuous, surrounding drivers, pedestrians, and other nearby individuals are not quickly aware of the need to clear a path to permit the emergency vehicle to race to the emergency. Therefore, an emergency light system for emergency vehicles is needed that is inconspicuous when the lights are off and conspicuous when the lights are on.

Another problem with the emergency lights behind the grille is installation. Generally, inconspicuous emergency vehicles are initially standard publicly sold vehicles that are retrofitted with emergency equipment. Retrofitting involves mounting brackets in locations not designed for supporting the brackets and other equipment behind the grille to support the lights and then installing the lights. This retrofitting sometimes leads to intended structural weaknesses in the grille and can be labor intensive if there is insufficient space behind the grille for mounting lights. Ideally, retrofitting is accomplished with minimal labor and without the installation of brackets and other materials where the environment is not designed for the installation.

SUMMARY OF THE INVENTION

The present invention is based on the realization that grilles for inconspicuous emergency vehicles can be designed by constructing automotive grilles with emergency lights built flush therein thereby allowing the lights to be unobstructed and conspicuous when lit and providing the opportunity to retrofit the grille with minimal effort.

Designing the grille with the emergency lights flush and inset therein will make the emergency vehicle more conspicuous when the lights are lit because the grille will not cover any portion of the flashing lights. Specifically, the design of the present invention will make the lights more conspicuous.

The present invention will make retrofitting vehicles easier. Because the lights are self-contained within the grille, no brackets or additional materials need to be installed. Ideally, the present design will allow a standard vehicle to be retrofitted with emergency lights simply by unscrewing the four screws holding the existing grille in place and screwing in the four screws to install the new grille.

Therefore, it is an object of the present invention to provide an inconspicuous emergency vehicle with emergency lights.

It is a further object of the present invention to enable the retrofitting of a vehicle with emergency lights with minimal labor.

BRIEF DESCRIPTION OF THE DRAWINGS.

These and other features and advantages of the present invention will be better understood by reading the following detailed description, taken together with the drawings wherein.

DETAILED DESCRIPTION OF THE INVENTION

Figure 1:
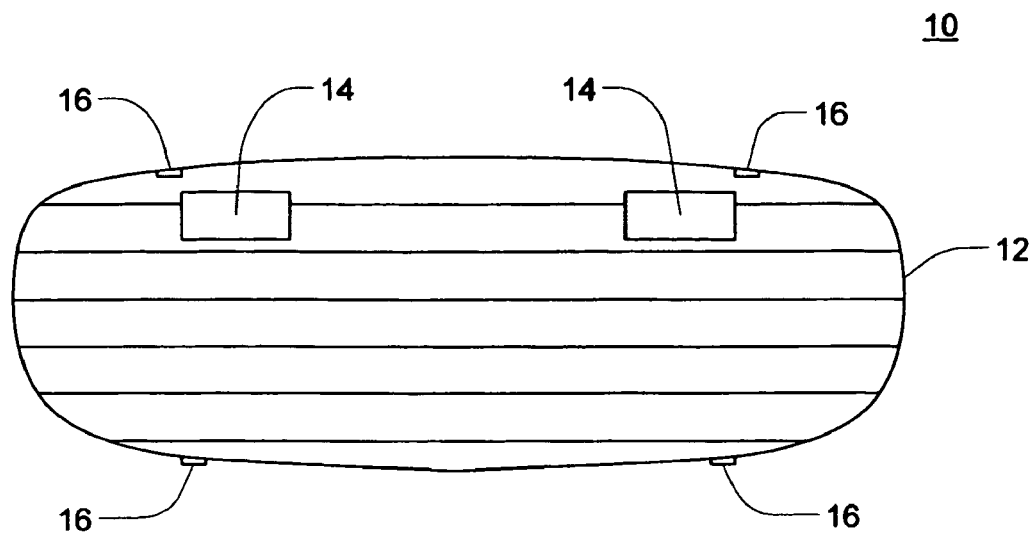
FIG. 1 shows a diagram of one embodiment of the present invention.
Figure 2:
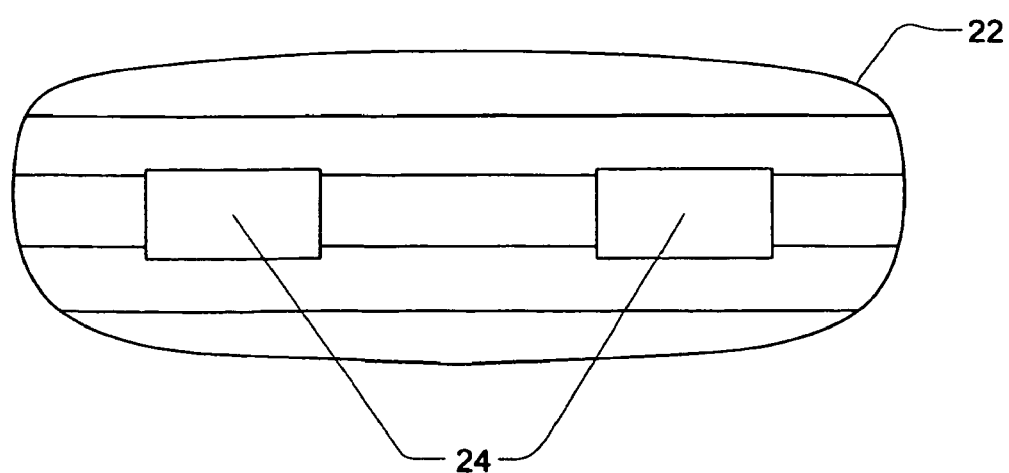
FIG. 2 shows a diagram of another embodiment of the present invention.

The present invention is a vehicular lighting system 10. The system includes a grille 12 and at least one light fixture 14 integrated with the grille 12 wherein the fixture 14 is unobstructed by the grille 12. The light fixtures 14 are fabricated in the grille 12 and the grille 12 is preformed to accept the light fixtures 14.

The light fixture 14 can be a strobe light, a halogen light, or a light emitting diode. In one embodiment, the grille 12 is substantially plastic, preferably 3/16" thick solid ABS, UV stabilized plastic. In another embodiment, the light fixture 14 is entirely supported by the grille 12, such that additional brackets do not need to be installed within the front of the automobile to support the light fixtures 14. Another embodiment involves having the front of the fixture 14 substantially flush with the front of the grille 12.

In one preferred embodiment, the vehicular lighting system is designed to be retrofitted to certain vehicles. Retrofitting a vehicle involves removing the vehicle's existing grille by removing the four screws attaching the grille to the vehicle. The inventive grille 12 is then installed using the same four screws to attach the grille 12 to the vehicle at the grille mounting holes 16. Other vehicles may be designed with different attachment means between the grille and vehicle, wherein the present inventive method would involve using an inventive grille 12 with similar attachment means without deviating from the scope of the present invention. The light fixtures 14 can be wired to a power source and a switch within the vehicle or battery-powered and initiated by a wireless switch or controlled and powered by other configurations that would be obvious to those skilled in the art.

The present invention, in a separate embodiment, is an emergency vehicle grille 20 made up of a grille base 22 having at least one unobstructed, preformed light fixture socket 24 for receiving a light fixture. As the industry recognizes standard light fixture sizes, designing a grille 20 to have only the socket 24 that conveniently accepts the standard light fixture sizes does not noticeably increase the labor required for installation. The standard light fixture surface area sizes are 3"×7". The sockets can also be built with an opening to accept a 3/16" cable for powering the fixtures.

Modifications and substitutions by one of ordinary skill in the art are considered to be within the scope of the present invention, which is not to be limited except by the following claims.

I claim:

1. A vehicular lighting system comprising:
   a grille; and
   at least one light fixture integrated with the grille wherein the fixture is unobstructed by the grille and the fixture is substantially flush with a front of the grille whereby said light fixture is inconspicuous until said light fixture is lit.

2. The system of claim 1 wherein the light fixture is a strobe light.

3. The system of claim 1 wherein the light fixture is a halogen light.

4. The system of claim 1 wherein the light fixture is a light emitting diode.

5. The system of claim 1 wherein the grille is substantially plastic.

6. The system of claim 1 wherein the light fixture is entirely supported by the grille.

7. An emergency vehicle grille comprising:
   a grille base having at least one unobstructed, preformed light fixture socket for receiving a light fixture, wherein the socket is formed in a three inch by seven inch opening in the grille base and wherein the light fixture received is substantially flush with a front of said grille base, whereby said light fixture is inconspicuous until said light fixture is lit.

* * * * *